(12) United States Patent
Giron et al.

(10) Patent No.: US 7,488,759 B2
(45) Date of Patent: Feb. 10, 2009

(54) MALIC ACID ADDITION SALTS OF TERBINAFINE

(75) Inventors: Danielle Giron, Mulhouse (FR); Jean-Louis Reber, Kembs (FR); Stefan Hirsch, Lörrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/606,268

(22) Filed: Nov. 29, 2006

(65) Prior Publication Data
US 2007/0088084 A1   Apr. 19, 2007

Related U.S. Application Data

(63) Continuation of application No. 10/470,885, filed as application No. PCT/EP02/01249 on Feb. 6, 2002, now abandoned.

(30) Foreign Application Priority Data
Feb. 7, 2001   (GB) ................... 0103046.9

(51) Int. Cl.
C07C 59/00   (2006.01)
A61K 31/135   (2006.01)
(52) U.S. Cl. .................. 514/649; 514/655; 562/578
(58) Field of Classification Search .................. 424/464, 424/484, 489; 514/655, 648, 649; 562/578
See application file for complete search history.

(56) References Cited

U.S. PATENT DOCUMENTS

| | | | |
|---|---|---|---|
| 3,507,755 A | 4/1970 | Bitners et al. | |
| 4,755,534 A | 7/1988 | Steutz | |
| 5,461,068 A | 10/1995 | Thaler et al. | |
| 5,817,875 A | 10/1998 | Karimian et al. | |
| 6,090,404 A | 7/2000 | Meconi et al. | |
| 6,121,314 A | 9/2000 | Richter et al. | 514/481 |

FOREIGN PATENT DOCUMENTS

| | | |
|---|---|---|
| CA | 2 285 368 | 10/1998 |
| EP | 0 024 587 | 3/1981 |
| EP | 0 024 788 | 3/1981 |
| EP | 0 053 518 | 6/1982 |
| EP | 0 244 944 | 11/1987 |
| EP | 0 318 860 | 6/1989 |
| EP | 0 515 310 | 11/1992 |
| EP | 0 515 312 | 11/1992 |

(Continued)

OTHER PUBLICATIONS

Kurabayashi et al., "Studies on the Alkaline Polymerization of Hydrogen Cyanide and its Inhibition. IV. Hazard Caused by the Effect of Water on it", Kogyo Kagaku Zasshi, vol. 71, No. 8, pp. 119-1123 (1968)—Caplus Abstract No. 1970:124810.

(Continued)

*Primary Examiner*—Taylor Victor Oh
(74) *Attorney, Agent, or Firm*—Leslie Fischer; Cozette M. McAvoy

(57) ABSTRACT

The invention concerns salts of the compound of formula I

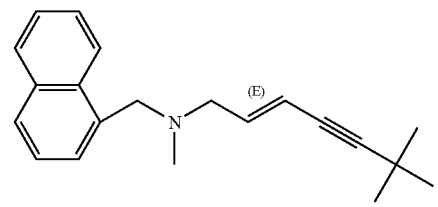

with malic acid, their preparation, corresponding pharmaceutical compositions and their use as antimycotics.

13 Claims, 6 Drawing Sheets

FOREIGN PATENT DOCUMENTS

| | | |
|---|---|---|
| EP | 0515310 | 11/1992 |
| EP | 1 222 160 | 7/2002 |
| GB | 2 041 372 | 9/1980 |
| JP | 2000-53681 | 2/2000 |
| JP | 2002-053462 | 2/2002 |
| JP | 2002-068974 | 3/2002 |
| JP | 2002-068975 | 3/2002 |
| WO | 98/43673 | 10/1998 |
| WO | 99/49835 | 10/1999 |
| WO | 99/49895 | 10/1999 |
| WO | 01/28976 | 4/2001 |
| WO | 01/95890 | 12/2001 |

OTHER PUBLICATIONS

Gould, Salt selection for basic drugs, Elsevier Science Publishers B.V., International Journal of Pharmaceutics, 33, p. 201-217 (1986).
Camille G. Wermuth, "The Practice of Medicinal Chemistry" (Japanese textbook), vol. 2, pp. 347-365, (1999).
Dr. M. Staehelin, "Affidavit of Friedrich Karl Mayer", (2007).
Hungarian Search Report dated Feb. 19, 2008 in corresponding Hungarian Patent Application No. P0303174.

MALIC ACID ADDITION SALTS OF TERBINAFINE

This application is a continuation of U.S. patent application Ser. No. 10/470,885, filed Feb. 18, 2004 now abandoned, which is a 371 of PCT International Application No. PCT/EP02/01249, filed Feb. 6, 2002.

The invention relates to acid addition salts of allylamine antimycotics.

It concerns salts of the compound of formula I

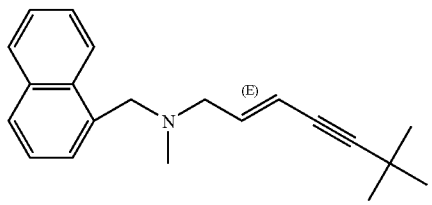

with malic acid,
i.e. (E)-N-methyl-6,6-dimethyl-N-(1-naphthylmethyl)hept-2-en-4-inyl-1-amine in malic acid addition salt form, hereinafter briefly named "the compounds of the invention".

The compounds of the invention are novel and improved pharmaceutical salts of the known compound of formula I.

A compound of the invention is in racemic or enantiomeric form. It is in malate or hydrogen malate, preferably in hydrogen malate, acid addition salt form. The malic acid moiety preferably is in racemic DL-(±)- or L-(−)-enantiomeric, especially in L-(−)-enantiomeric form. Particularly preferred are thus the DL-(±)- and the L-(−)-, especially the L-(−) -hydrogen malate.

The compounds of the invention exhibit polymorphism. The invention includes the compounds of the invention in any polymorphic form, e.g. form A or form B of the L-(−)-hydrogen malate as described hereunder.

The invention also includes a process for the preparation of a compound of the invention which comprises reacting the compound of formula I in free base form with an appropriate malic acid form and recovering from the reaction mixture the resultant salt.

The process of the invention may be effected in conventional manner, e.g. by reaction in an appropriate inert solvent such as isopropanol, acetic acid ethyl ester, isopropyl acetate, cyclopentanone, n-butanol or ethyl formate.

The compound of formula I in hydrochloric acid addition salt form and its use as an antimycotics e.g. in the treatment of mycosis caused by dermatophyte infection, is known i.a. from EP 24687 and its equivalents. It is available in free base or hydrochloric acid addition salt form under the trademark Lamisil®, with the generic name terbinafine. Two further salt forms have also been mentioned in the literature, e.g. in EP 515310A1, the lactate and the ascorbate, in relation with pharmaceutical compositions for topical application on skin.

Terbinafine is an orally and topically effective anti-fungal agent. It is effective in a wide range of fungal diseases, including i.a. fungal sinusitis infection and onychomycosis. It is particularly useful against dermatophytes, contagious fungi that invade dead tissues of the skin or its appendages such as stratum corneum, nails, and hair. Such a nail fungus makes its home in the nail bed, shielded by the hard outer nail. Thus once infection is established under the nail, the nail itself provides the fungus with a protected environment that allows it to grow. The effects of these fungi on the nails may be unsightly, they seriously complicate foot-care, have a deleterious impact on the patient's overall quality of life and well-being and impair the patient's ability to work. If left untreated, the fungi can deform toenails permanently and lead to pain on walking. Additionally the fungi can lead to fissures in the skin encouraging bacterial infections. Serious complications as a result of these infections may occur in people suffering from diabetes such as diabetic foot syndrome including primary disease-related complications, e.g. gangrene that, ultimately, can be life-threatening or require amputation. Other high-risk patient sub-groups include patients infected with human immunodeficiency virus (HIV), patients with acquired immunodeficiency syndrome (AIDS), and patients with other types of immunosuppression (e.g. transplant recipients and patients on long term corticosteroid therapy). There is an increased prevalence of onychomycosis in the elderly (up to 30% by age 60). Microsporum, *Trichophyton* such as *Trichophyton rubrum* or *Trichophyton mentagrophytes*, and *Epidermophyton* such as *Epidermophyton floccosum* are those fungi commonly involved. Across medical disciplines, onychomycosis is well recognized as being arduous both to diagnose and to manage, particularly in the aged.

Terbinafine is also useful to treat toenail and fingernail onychoinycosis (e.g. *Tinea unguium*) due to dermatophytes. Indeed terbinafine has opened up treatment for *Tinea unguium* caused by *Trichophyton*. For example it has been stated that treatment of toenails should be discouraged with the previously used standard, griseofulvin, because 1 to 2 years treatment is required, recurrence is usual and complete cure unlikely.

For the oral use in onychomycosis, terbinafine hydrochloride is normally administered as an immediate release tablet form containing 250 mg terbinafine once daily. Such a tablet, sold under the trademark Lamisil® releases terbinafine to the extent of 80% over a 30 minute period as measured by standard in vitro dissolution studies, e.g. at pH 3 using the paddle method. Terbinafine treatment over 12 weeks is required. The progress of its clinical effectiveness is seen with growth of the healthy nail, pushing out and replacing the diseased unsightly nail containing debris and dead fungus. About 10 months is needed for a totally new toenail to form.

Although terbinafine is generally regarded to be as safe as any prescription drug, adverse events associated with its use have been reported. There have been a number of adverse events recorded, e.g. headaches, gastrointestinal symptoms (including diarrhea, dyspepsia, abdominal pain, nausea and flatulence), liver test abnormalities, e.g. enzyme abnormalities, dermatological symptoms such as pruritis, urticaria and rashes, and taste disturbances, e.g. loss of taste. These adverse events are in general mild and transient. Further adverse events include symptomatic idiosyncratic hepatobiliary dysfunction (e.g. cholestatic hepatitis), severe skin reactions such as Stevens-Johnson syndrome, neutropenia, and thrombocytopenia. Yet further adverse events may include visual disturbances such as changes in the ocular lens and retina, as well as allergic reactions including anaphylaxis, fatigue, vomiting, arthralgia, myalgia and hair loss. Terbinafine is a potent inhibitor of CYP2D6 and may cause clinically significant interactions when co-administered with substrates of this isoform, such as nortriptyline, desipramine, perphenazine, metoprolol, encainide and propafenone. Hereinafter any and all these events are referred to briefly as Adverse Events.

Pharmacokinetic and biopharmaceutical properties of terbinafine hydrochloride are known. Thus it is well absorbed. Peak drug plasma concentrations (hereinafter $C_{max}$) of about 1.3 μg/ml (with about a 20% variation, e.g. 0.9 to 1.6 μg/ml)

appear in human subjects within 1 to 2 hours after administration of a single 250 mg terbinafine dose. The area under the curve over 24 hours (hereinafter AUC) is about 4.76 μg·hour/ml. The increase in AUC is 42% when terbinafine is administered with a fat-rich meal. In patients with renal impairment (e.g. creatinine clearance≧50 ml/min) or hepatic cirrhosis, the clearance of terbinafine is reduced by approximately 50%. In the steady state, e.g. when the trough and peaks are constant after several days dosing, in comparison to the single dose, $C_{max}$ is 25% higher and the AUC increases by a factor of 2.5. This is consistent with an effective half-life for terbinafine of about 36 hours.

Pharmacokinetic and absorption properties have been disclosed e.g. in J. Faergemann et al., *Acta Derm. Venereol.* (Stockh.) 77 (1997) 74-76. The site of absorption of terbinafine is, however, not known and there is no clinically proven correlation of effect with pharmacokinetic profile, so there is no rational starting point for developing pharmaceutical forms containing terbinafine with improved therapeutic effects.

Despite the very major contribution which terbinafine has made, the reported occurrence of undesirable Adverse Events has been an impediment to its wider oral use or application. The particular difficulties encountered in relation to oral dosing with terbinafine hydrochloride have inevitably led to restrictions in the use of terbinafine therapy for the treatment of relatively less severe or endangering disease conditions, e.g. *Tinea pedis*.

It has now been found that, unexpectedly, salts of the compound of formula I with malic acid possess particularly beneficial pharmacokinetic properties, and have further been found to possess a unique combination of favourable formulation properties which make them particularly suitable for the preparation of pharmaceutical compositions of terbinafine adapted for systemic and topical administration.

Thus the variability of pharmacokinetic parameters is considerably less when a malate salt of the compound of formula I is employed systemically than with known salts or the free base, e.g. the hydrochloride.

This appears i.a. from a pharmacokinetic study in animals involving 7 Beagle dogs weighing about 10 kg, aged about 5 years, upon oral administration of capsules prepared by mixing active terbinafine salt substance [hydrochloride or L-(−)-hydrogen malate; 62.5 mg base equivalent per capsule] with lactose in a ratio of 1:1 w/w and filling into appropriate hard gelatine capsules (particle size distribution similar for both salts).

The inter-animal variability in plasma exposure of terbinafine (as expressed by the coefficient of variation [hereinafter CV] of the area-under-the-curve [AUC] has been found to be distinctly reduced when the L-(−)-hydrogen malate salt of terbinafine is administered, namely 30%, as compared with 39% with the hydrochloride. The mean AUC values obtained thereby were, respectively, 392 and 348 ng.hour/ml, showing even a slight increase in absolute plasma exposure with the hydrogen malate salt.

The mean $C_{max}$ values obtained thereby are 134 and 146 ng/ml for the L-(−)-hydrogen malate and the hydrochloride, respectively, with corresponding CV values 26% and 47%, respectively, a further indication of reduced variability of pharmacokinetic parameters when a malate salt is used.

It can be expected therefrom that in human subjects, a similarly reduced variability of pharmacokinetic parameters is obtained, and thus even more stable efficacy of treatment with terbinafine in antimycotic indications may be envisaged, even at very high dosages, in particular upon oral administration, e.g. in the oral treatment of onychomycosis.

Further, the compounds of the invention may also be employed topically, e.g. on the nail, as appears for example from the following in vitro penetration/permeation assay:

Human cadaveric toe nails are used in a Franz cell (FIG. 1) modified to accept cadaveric human toenails by having a pair of flexible rings made of a silicone elastomer (PDMS) having good sealant properties to adequately mount hard nails, using liquid scintillation counting (LSC) (picogram limit of detection) to measure the increase in radioactivity in the acceptor compartment. Each measurement is effected in triplicate. 90 randomly selected nails are exposed for 72 hours to a solution of 100 μl of $^{14}$C-labelled terbinafine hydrochloride or terbinafine L-(−)-hydrogen malate (form A) solution [25 μBq/ml; 1% active product; 5% 1,2-propylene glycol; 2% Cetomacrogol-1000® (polyoxyethylene-glycol-1000-monoacetylether); 25% ethanol 94%; 67% distilled water] (w/w). Each area of the nail exposed to the formulation has a 9 mm diameter (about 64 mm$^2$). Exposure is effected under occlusive (chamber closed to air) and non-occlusive (chamber open to air) conditions.

The radiolabelled product is detectable in the buffer-filled receptor chamber from about 8 hours of incubation. Its concentration in the receptor chamber as measured by LSC increases with incubation time and concentration of applied formulation. A total of 24 penetration chambers are used in parallel. Each formulation is measured in triplicate.

The result is as appears from FIG. 2: under both occlusive (black dots) and non-occlusive (black squares) conditions, at 72 hours substantial permeation is observed (about 63 ng and 41 ng, respectively).

Further, it has been found that the compounds of the invention surprisingly possess favourable formulation properties. They thus form crystals more readily than the hydrochloride or the free base. Further, the crystals of e.g. the L-(−)-hydrogen malate salt exhibit various polymorphic forms. Polymorphs have different dissolution rates, milling behaviour and stability, e.g. in galenical forms where the pharmaceutically active compound is in solid form, such as tablets or suspensions, and they influence bioavailability. The surprising presence of polymorphism is therefore advantageous in terms of improved processability, such as with polymorph particularly stable thermodynamically, in formulations with compound in solid form, e.g. tablets or suspensions, or with polymorph having a particularly high dissolution rate or solubility, in formulations with dissolved compound, e.g. nail lacquers. The compounds of the invention are therefore better processable for e.g. large scale tablet formulation; they also have favourable penetration/permeation properties and can thus readily be formulated into topical forms, such as nail lacquers. Additionally, they possess good solubility in water and many organic solvents, a prerequisite for good bioavailability: thus at 25° C., the L-(−)-hydrogen malate is soluble up to about 12-15 mg/ml in water and >30 mg/ml in ethyl acetate, as compared with 6.7 mg/ml in water and 0.7 mg/ml in ethyl acetate for the hydrochloride. Further, they are non-hygroscopic, thus providing stable formulations while minimizing the risk of intrinsic chemical breakdown.

They therefore show a unique combination of good processability, good solubility and non-hygroscopicity which makes them remarkably suitable for the preparation of pharmaceutical compositions of terbinafine.

The invention further includes:
  a pharmaceutical composition comprising a compound of the invention together with at least one pharmaceutically acceptable carrier or diluent;
  a pharmaceutical composition comprising the compound of formula I in free form or pharmaceutically acceptable salt form other than a malic acid addition salt form, whenever prepared from a compound of the invention;

a compound of the invention for use as a pharmaceutical;

a compound of the invention for use in the preparation of a medicament;

a compound of the invention whenever prepared by a process as defined above;

a compound of formula I in free base form or salt form other than a malic acid addition salt form, whenever prepared from a compound of the invention;

the use of a compound of the invention in the preparation of a medicament for the treatment, e.g. orally, of diseases susceptible of therapy with the compound of formula I in free base form or salt form, such as fungal diseases;

a process for the preparation of a pharmaceutical composition which comprises mixing a compound of the invention together with at least one pharmaceutically acceptable carrier or diluent; and a method for the prophylactic or curative treatment of fungal diseases such as fungal sinusitis infection or onychomycosis, comprising administration of a therapeutically effective amount of a compound of the invention to a subject in need of such treatment.

Pharmaceutical compositions incorporating a compound of the invention are preferably compounded in unit dosage form, e.g. by filling into capsule shells, e.g. soft or hard gelatine capsule shells, or by tabletting or some other moulding process. Thus unit dosage forms suitable for administration once or twice daily, e.g. depending on the particular purpose of therapy, the phase of therapy, etc., will appropriately comprise half or the total daily dose contemplated. Such compositions may be administered twice or three times a week. Preferably the compositions are administered once-a-day.

The amount of compound of the invention will of course vary, e.g. depending on to what extent other components are present, the mode of administration and the treatment desired. In general, however, it will be present in an amount within the range of from about 0.1% to about 35% by weight based on the total weight of the composition. The total daily dosage of active compound (expressed in free base equivalent) is, for example, from about 50 mg to about 500 mg daily, e.g. 250 mg daily, or 400 mg, 600 mg or 700 mg daily, conveniently given, for example, in divided doses up to 4 times a day. Unit dosage forms comprise e.g. from about 12.5 mg to about 800 mg of compound of the invention (expressed in free base equivalent) in admixture with at least one solid or liquid pharmaceutically acceptable carrier or diluent.

The compounds of the invention may be administered in similar manner to known standards for use in such indications.

They may be admixed with conventional, chemotherapeutically acceptable carriers or diluents and optionally further excipients, and administered e.g. orally, e.g. in the form of formulations such as tablets and capsules. A preferred tablet formulation includes a compound of the invention, a compression aid such as microcrystalline cellulose, an additive to provide sheen to the tablet such as anhydrous dibasic calcium phosphate, a disintegrant such as sodium starch glycolate; and a lubricant such as magnesium stearate. A preferred capsule formulation includes a compound of the invention, an inert diluent, a dried disintegrant and a lubricant as described above.

Alternatively, they may be administered topically, e.g. in the form of formulations, e.g. lotions, solutions, ointments or creams, such as nail lacquers, or parenterally or intravenously. The concentration of active substance will of course vary, e.g. depending on the compound of the invention employed, the treatment desired and the nature of the form or formulation used. In general, satisfactory results are obtained in e.g. topical formulations at concentrations of from about 0.1% to about 10%, particularly from about 0.5% to about 2%, especially about 1% by weight.

With the present invention there are thus also provided novel terbinafine compositions containing the compounds of the invention which meet or substantially reduce the difficulties in terbinafine therapy hitherto encountered. In particular they may contain terbinafine in sufficiently high and constant concentrations to permit convenient oral once-a-day administration, while at the same time achieving improved safety and tolerability in terms of fewer Adverse Events.

Thus the present invention enables reduction of terbinafine treatment times required to achieve effective therapy, reducing the exposure time to terbinafine and improving the global safety profile. In addition it allows closer standardization as well as optimization of on-going daily dosage requirements for individual subjects receiving terbinafine therapy as well as for groups of patients undergoing equivalent therapy. By closer standardization of individual patient therapeutic regimens, dosaging parameters for particular patient groups as well as monitoring requirements may be reduced, thus substantially reducing the cost of therapy.

Further pharmacokinetic properties of pharmaceutical compositions containing the compounds of the invention may be determined in standard animal and human pharmacological (bioavailability) trials. For example one standard pharmacological trial may be carried out in healthy male or female non-smoking volunteers aged between 18 to 45 years having within 20% of the ideal body weight. The trial may be a single-dose crossover application. The subjects are domiciled for 24 hours. Blood samples are taken for 1, 2, 4, 8, 16, 32 and 72 hours after administration of a pharmaceutical composition containing a compound of the invention and tested for terbinafine. Terbinafine blood or plasma concentrations may be determined in conventional manner, e.g. by HPLC/UV or LC-MS analytical techniques. Safety is judged according to a standard checklist based on Adverse Event symptoms after 1 week. Preferably the dose of terbinafine salt is 400, 600 or 700-800 mg of base equivalent per day. The safety of terbinafine at such a dose over the short duration of treatment is remarkable. The oral compositions of the invention preferably exhibit a $C_{max}$ of 100-250%, e.g. 100-150%, of that shown by 250 mg immediate release terbinafine hydrochloride tablets, e.g. administered as a single dose and/or in the steady state, e.g. once a day for 7 days.

Pharmacokinetic drug skin and nail concentration studies may be carried out according to the same principles as set out for the above-mentioned standard pharmacological trials. For example a clinical trial may be effected with daily dosing of compositions containing a compound of the invention over a 3-week treatment period.

Tablets containing the compounds of the invention are useful for the same indications as for known immediate release terbinafine hydrochloride tablets. The utility of compounds of the invention may be observed in standard clinical tests or standard animal models. For example, one can ascertain dosages of compositions containing a compound of the invention giving AUC plasma levels of terbinafine equivalent to AUC plasma levels giving a therapeutic effect on administration of known terbinafine hydrochloride oral dosage forms, e.g. a tablet. Pharmaceutical compositions containing a compound of the invention are particularly and surprisingly well-tolerated with regard to the Adverse Events mentioned above, they provoke fewer Adverse Events when co-administered with CYP2D6 substrates such as nortriptyline, desipramine, perphenazine, metoprolol, encainide and propafenone.

A randomized double-blind positive-controlled and placebo-controlled study may e.g. be effected with subjects having onychomycosis of the toenail confirmed by microscopy and culture. Treatment is carried out over 12 weeks. Clinical trials may be effected in several hundred patients to ascertain the freedom from Adverse Events. However, therapeutic efficacy may already be shown in trials with 25 patients aged over 12 years. Safety is evaluated by an Adverse Event report of clinical aspects and vital signs. Efficacy is determined by microscopy, culture procedures and visually looking at signs and symptoms. Efficacy is seen in patients with the fungi described above, especially *Trichophyton rubrum*, *Trichophyton mentagrophytes* and *Epidermophyton floccosum*. Patients include those with predisposing factors such as impaired blood circulation, peripheral neuropathy, diabetes mellitus, damage from repeated minor trauma, and limited immune defects as well as AIDS. Patients have (i) distal lateral subungual onychomycosis, starting at the hyponychium spreading proximally to the nail bed and matrix, (ii) proximal subungual onychomycosis, wherein the fungus infects the cuticle and eponychium to reach the matrix where it becomes enclosed into the nail plate substance, (iii) total dystrophic onychomycosis, and (iv) superficial white onychomycosis. If desired plasma concentrations of terbinafine may be evaluated in conventional manner or as described herein. Concentrations of terbinafine in the nail may be evaluated from nail clipping followed by analysis.

EXPLANATION OF THE FIGURES

In FIGS. 3 to 6: cps=signal intensity (counts per second); Deg.=angle of diffraction (degrees).

The following Examples illustrate the invention. All temperatures are in degrees Celsius. m.p.=melting point.

EXAMPLE 1

Terbinafine L-(−)-hydrogen malate (polymorph form A)

15.54 g (53.32 mmoles) terbinafine base and 6.79 g (50.65 mmoles) L-(−)-malic acid are dissolved in 125 ml of ethyl acetate at 60°. The solution is cooled to 0° and slow crystallisation takes place. After 2 days standing at 4° only a few crystals have precipitated. The mixture is then stirred at 0°. After 8 hours stirring the thick suspension is diluted with 50 ml of ethyl acetate. The mixture is filtered. Filtration is very slow. The cake is washed with 60 ml of ethyl acetate at 0° and dried at 50°/10 mbar for 20 hours. The title compound in form A is obtained (fine white powder; m.p. ~96°; solubility at 25°: in ethanol, ethane/water 2:8 v/v, and ethyl acetate>30 mg/ml; in water ~12 mg/ml):

Elementary Analysis: Calc.: 70.57% C, 7.34%; H, 3.29%; N, 18.80% O. Found: 70.35% C, 7.39%; H, 3.13%; N, 18.94% O.

Figure 1:
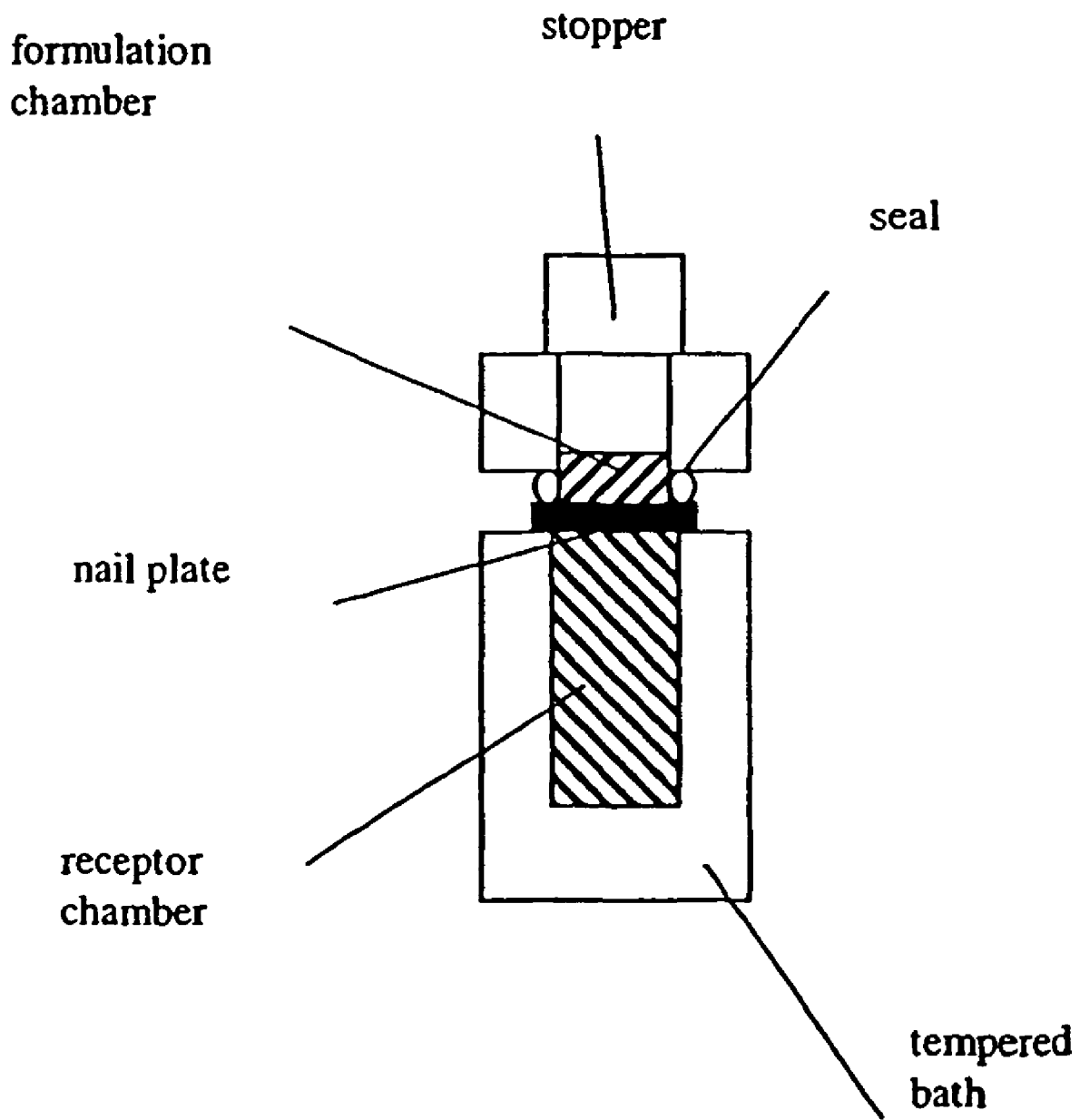
FIG. 1: Schematic representation of a Franz cell.
Figure 2:
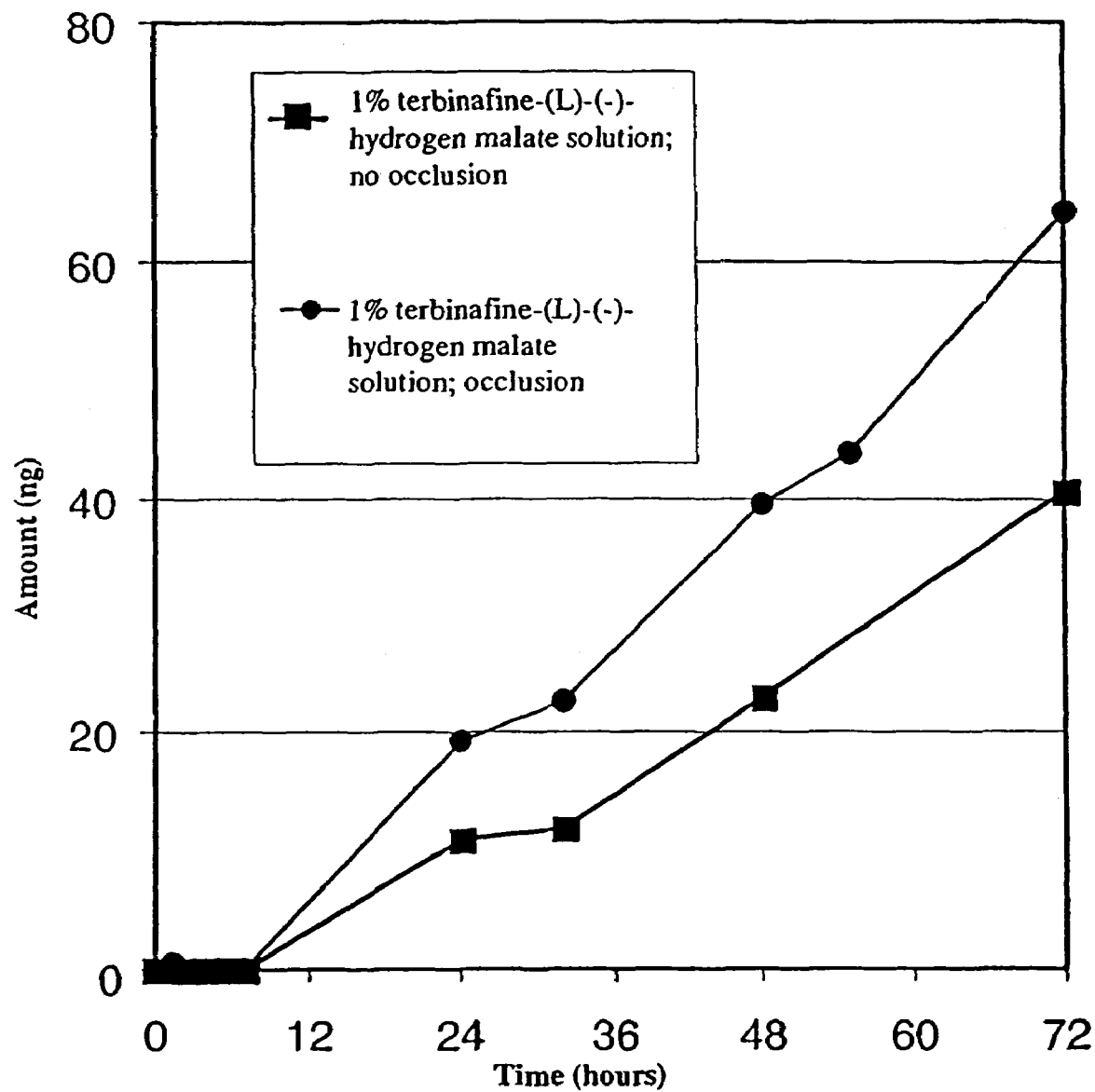
FIG. 2: Penetration/permeation assay: amount recovered in receptor chamber (in ng) vs. time (in hours) with 1% terbinafine-(L)-(−)-hydrogen malate solution: black squares: no occlusion conditions; black dots: occlusion conditions.
Figure 3:
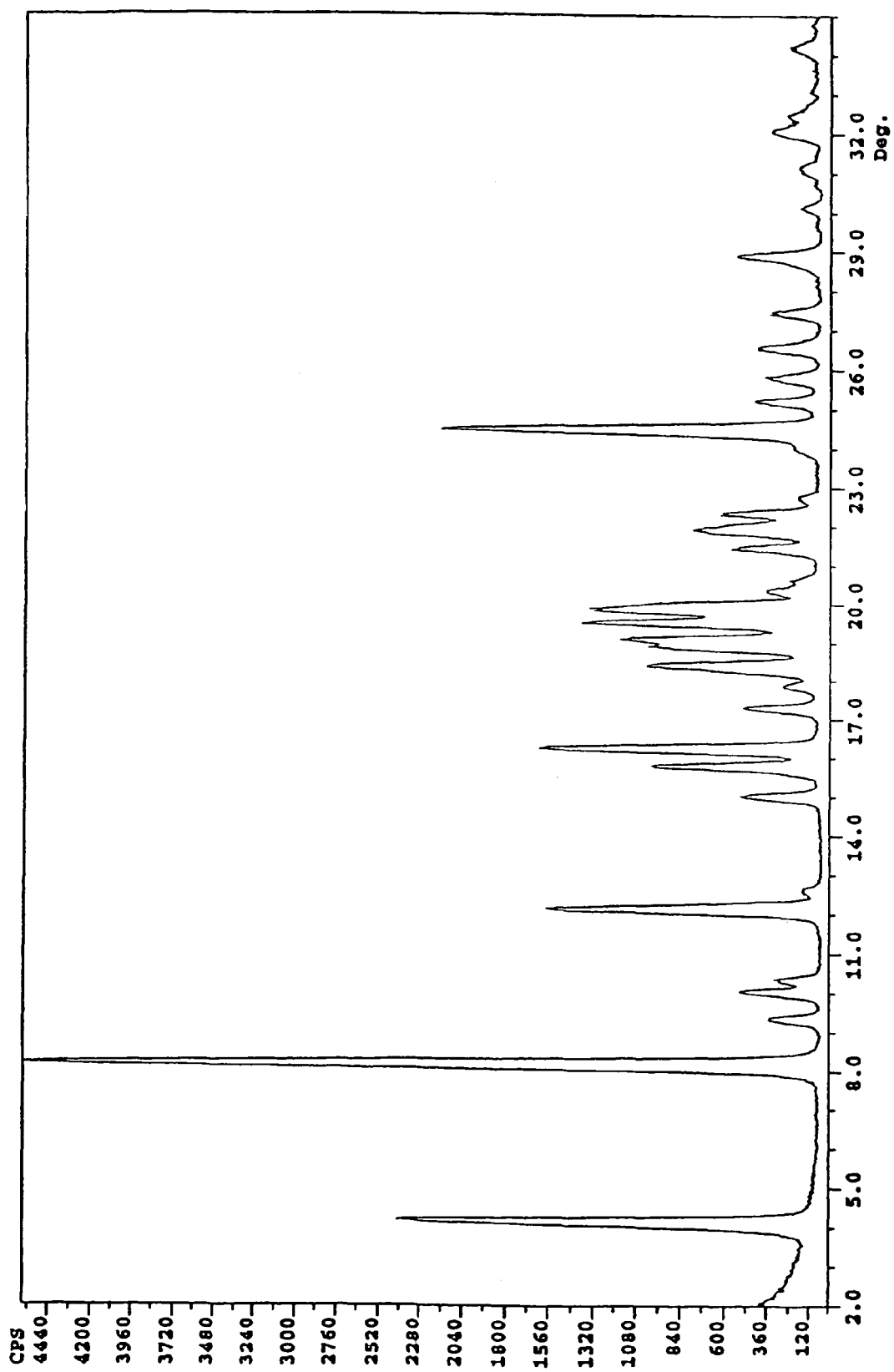
FIG. 3: X-ray powder diffraction pattern with terbinafine L-(−)-hydrogen malate polymorph form A (Examples 1 and 3).

X-ray powder diffraction pattern: see FIG. 3.

EXAMPLE 2

Terbinafine L-(−)-hydrogen malate (polymorph form B)

200.0 g terbinafine base (686.2 mmoles) and 92.02 g L-(−)-malic acid are dissolved in 1500 ml of ethyl acetate at 60°. The clear solution is then allowed to slowly cool down. 29.2 g terbinafine L-(−)-hydrogen malate form B seed crystals (obtained as described hereunder) is added at 32° and the suspension stirred at room temperature (20-25°) for 20 hours. The mixture is then cooled to 3° over 2 hours and stirred for 4 hours at that temperature. The resultant precipitate is filtered. The crystals are dried at 50° and 10 mbar for 20 hours. The title compound in form B is obtained (white powder; m.p.: ~96°; solubility at 25° in water: 15 mg/ml; $[\alpha]^{20}$ at 365 nm=+7.2° in methanol) (as a control of the positive rotation value, 100 mg salt obtained is dissolved in 2 ml of methylene chloride, 3 ml NaOH 0.2 N is added, and the rotation value of the aqueous phase containing free L-(−)-malic acid is measured: $\alpha^{20} = -0.134°$ at 546 nm):

Elementary Analysis: Calc.: 70.57%; C, 7.34%; H, 3.29%; N, 18.80% O. Found: 70.54%; C, 7.37%; H, 3.26%; N, 18.75% O.

Figure 4:
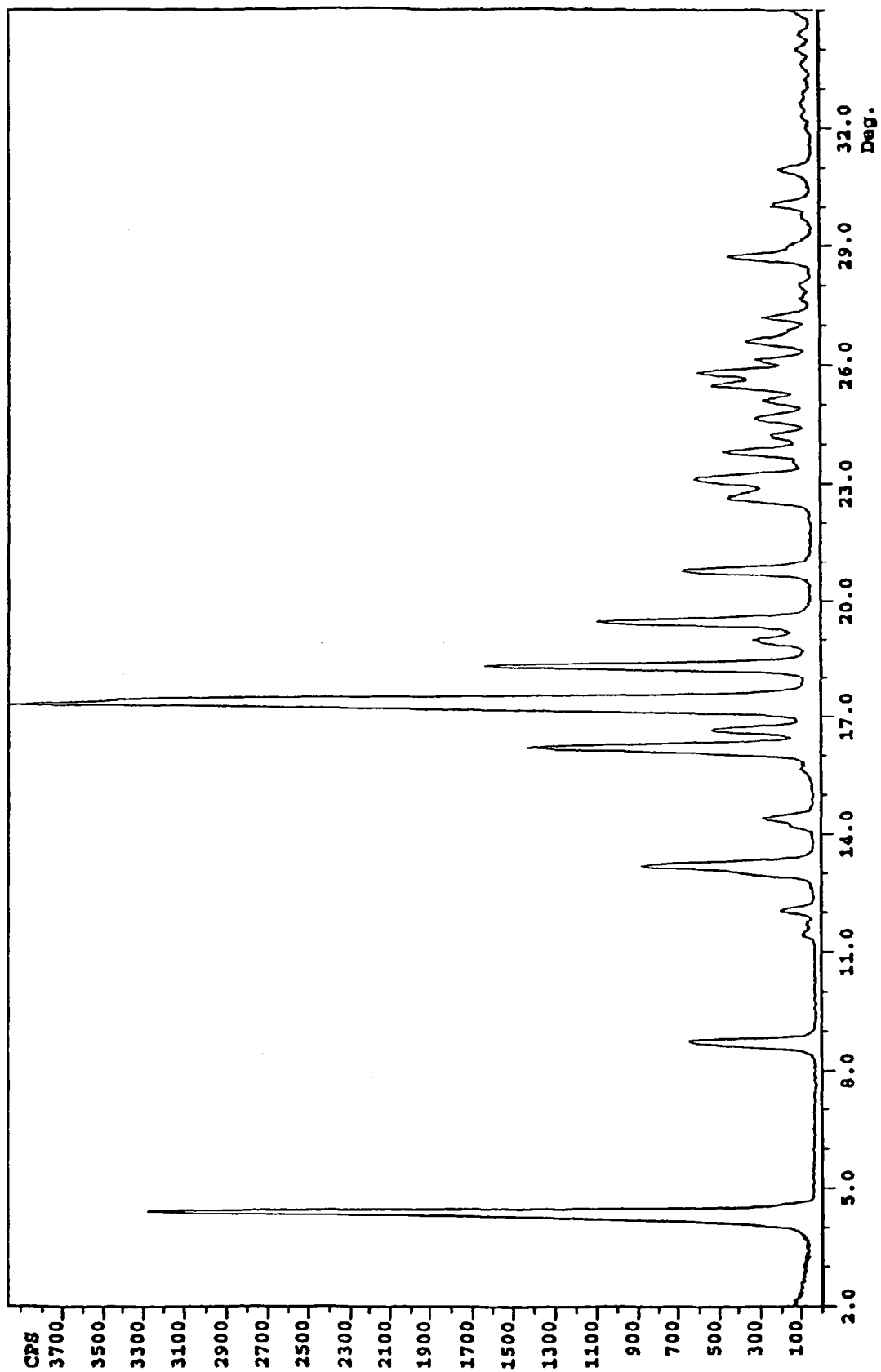
FIG. 4: X-ray powder diffraction pattern with terbinafine L-(−)-hydrogen malate polymorph form B (Example 2).

X-ray powder diffraction pattern: see FIG. 4.

Seed crystals of form B are obtained as follows:

19.57 g terbinafine base and 8.55 g L-(−)-malic acid are dissolved in 160 ml of ethyl acetate at 50°, the solution is then cooled to 25° over a period of 1 hour, and seeded with 5 mg terbinafine L-(−)-hydrogen malate (form A) crystals obtained as described in Example 1; the resultant mixture is allowed to stay unstirred overnight for 18 hours, then slowly stirred at room temperature; the resultant gelatinous mixture is warmed to 50° and the resultant clear solution then cooled to 25° and inoculated again, with 10 mg terbinafine-L-(−)-hydrogen malate form A crystals; the mixture is allow to rest for 3 days at room temperature without stirring. The resultant mixture is then gently stirred again and crystallization slowly sets in. After 24 hours further stirring at room temperature, the mixture is stirred for 3 hours at 3°, filtered and dried. Crystalline terbinafine-L-(−)-hydrogen malate form B is obtained.

EXAMPLE 3

Terbinafine L-(−)-hydrogen malate (polymorph form A)

400.0 g terbinafine base (1.3725 moles) and 180.34 g L(−)-malic acid (1.3450 moles) are dissolved in 3200 ml of isopropanol at 35°. The solution is cooled to 25° over 45 minutes and seeded with 5.72 g terbinafine-L-(−)-hydrogen malate form A (obtained as described in Example 1). After 27 hours stirring at room temperature the thick suspension is filtered. Filtration is slow. The crystals are washed with 500 ml of isopropanol and dried at 50°/15 mbar for 24 hours. The title compound in form A is obtained (fine white powder; m.p. ~96°; solubility at 25°; in ethanol>50 mg/ml, ethylacetate>30 mg/ml; in water ~12 mg/ml):

Elementary Analysis: Calc.: 70.57%; C, 7.34%; H, 3.29%; N, 18.80% O. Found: 70.47%; C, 7.12%; H, 3.40%; N, 18.60% O.

X-ray powder diffraction pattern: see FIG. 3.

EXAMPLE 4

Terbinafine D-(+)-hydrogen malate 8.70 g (29.8 mmoles) terbinafine base and 4.00 g (29.8 mmoles) D(+)-malic acid are dissolved in 100 ml of ethyl acetate at 50°. The clear solution is allowed to slowly cool down and 254 mg terbinafine-D-(+)-hydrogen malate seed crystals (obtained as described hereunder) is added at 25°. Slow crystallization takes place and the mixture is stirred at room temperature (20-25°) for 63 hours. The thick suspension is filtered. Filtration is very slow. The filter cake is washed with 20 ml of ethyl acetate and dried at 50°/10 mbar for 20 hours. The title compound is obtained (m.p. ~96°; solubility in water at 25°: ~7 mg/ml, supersaturation; $[\alpha]^{20}$ at 365 nm=−7.0° in methanol) (as a control of the negative rotation value, 100 mg salt obtained is dissolved in 2 ml of methylene chloride, 3 ml NaOH 0.2 N is added, and the rotation value of the aqueous phase containing free D-(+)-malic acid is measured: $\alpha^{20}$=+0.137° at 546 nm):

Elementary Analysis: Calc.: 70.57%; C, 7.34%; H, 3.29%; N, 18.80% O. Found: 70.42%; C, 7.45%; H, 3.20%; N, 18.92% O.

Figure 5:
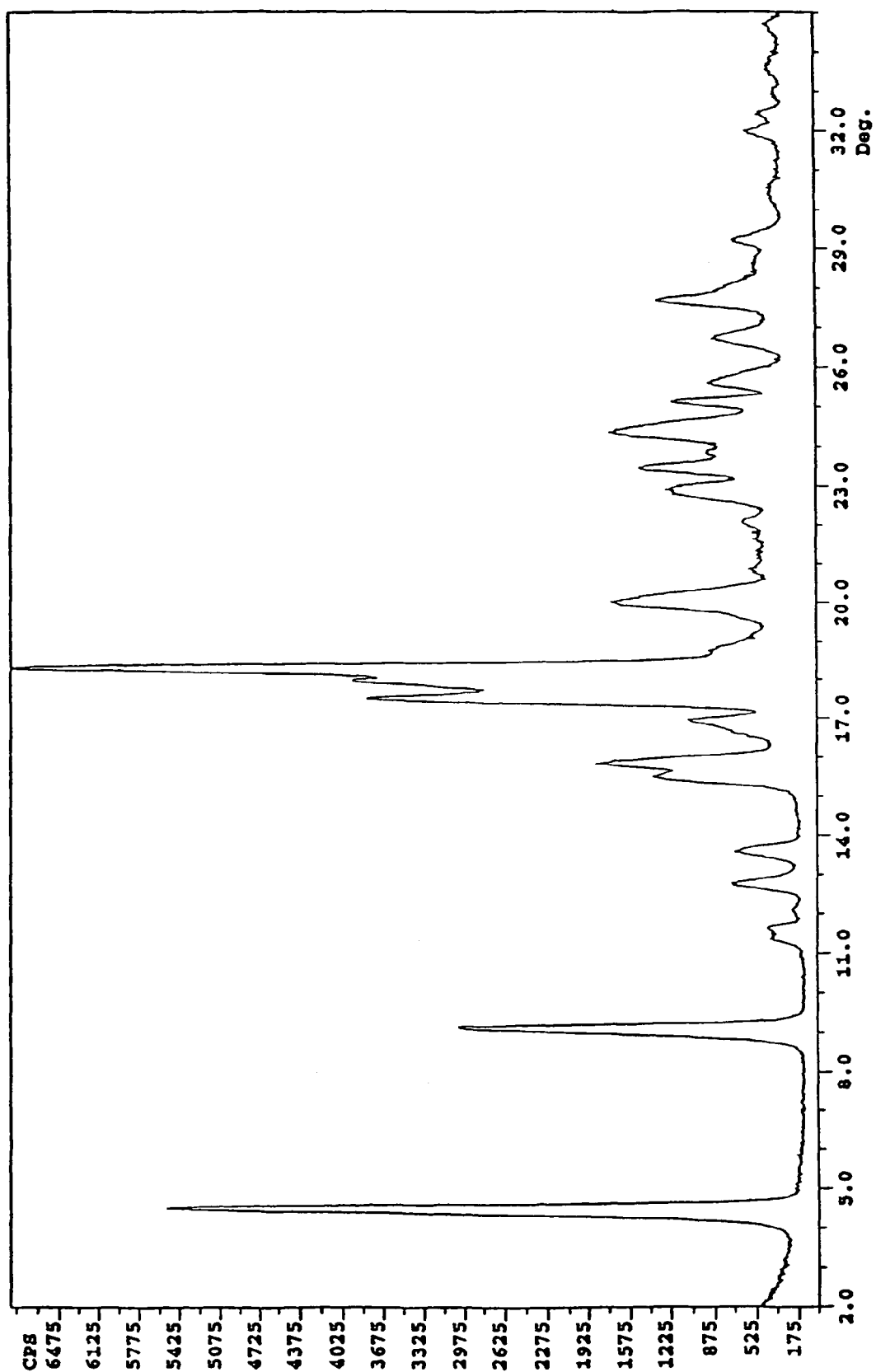
FIG. 5: X-ray powder diffraction pattern with terbinafine D-(+)-hydrogen malate (Example 4).

X-ray powder diffraction pattern: see FIG. 5.

Seed crystals are prepared as follows:

4.35 g terbinafine base and 2.00 g D(+)-malic acid are dissolved in 35 ml of isopropanol at 80°. The solution is cooled to 25° over a period of 30 minutes, and seeded with 20 mg terbinafine-DL-(±)-malate (obtained as described in Example 5). A very slow crystallization process takes then place. After two days stirring at room temperature only a small amount of crystals has precipitated. The suspension is filtered and the cake is washed with 5 ml of isopropanol. The crystals are dried at 50°/10 mbar for 20 hours. Crystalline terbinafine-D-(+)-hydrogen malate in obtained.

EXAMPLE 5

Terbinafine DL-(±)-hydrogen malate

A suspension of 8.70 g terbinafine base (29.8 mmoles) and 4.00 g DL-malic acid (29.8 mmoles) in about 70 ml of isopropanol is heated to 80° and a clear solution is obtained. The solution is allowed to slowly cool down. 10 mg terbinafine-L-(−)-hydrogen malate (polymorph form A, obtained as described in Example 1) are added at 25°. The mixture is stirred for 7 hours at room temperature. The resultant precipitate is filtered and the filter cake is washed with 30 ml of isopropanol. The crystals are dried at 50°/10 mbar for 20 hours. The title compound is obtained (white powder, m.p. ~107°; solubility at 25°: in ethanol >50 mg/ml; in ethyl acetate ~17 mg/ml; in water ~7 mg/ml):

Elementary Analysis: Calc.: 70.57%; C, 7.34%; H, 3.29%; N, 18.80% O. Found: 70.49%; C, 7.36%; H, 3.16%; N, 18.82% O.

Figure 6:
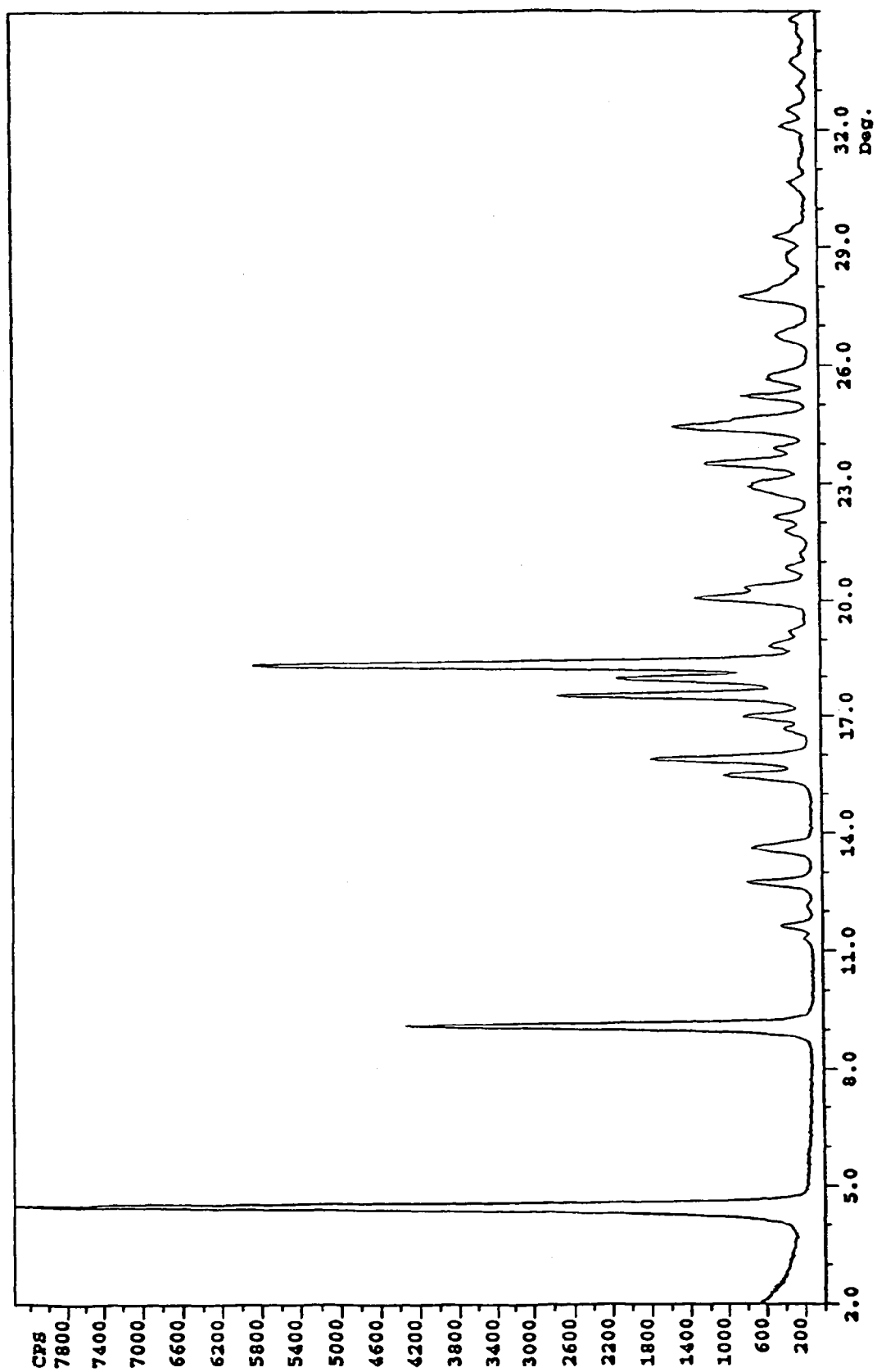
FIG. 6: X-ray powder diffraction pattern with terbinafine DL-(±)-hydrogen malate (Example 5).

X-ray powder diffraction pattern: see FIG. 6.

The invention claimed is:

1. A salt of the compound of formula I

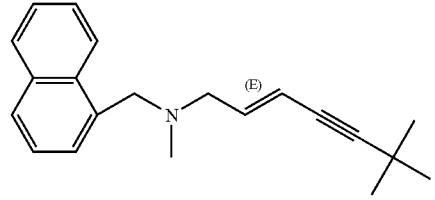

with malic acid.

2. A compound according to claim 1 in the form of the L-(−)-hydrogen malate.

3. A process for the preparation of a compound according to claim 1 which comprises reacting the compound of formula 1 in free base form with an appropriate malic acid, said appropriate malic acid selected from the group consisting of L-(−)-malic acid, D-(+)-malic acid and DL-(±)-malic acid and recovering from the reaction mixture the resultant salt.

4. A pharmaceutical composition comprising a compound according to claim 1 together with at least one pharmaceutically acceptable carrier or diluent.

5. A pharmaceutical composition comprising the compound of formula 1 in free base form or pharmaceutically acceptable salt form other than a malic acid addition salt form, whenever prepared from a compound according to claim 1.

6. A method of treating fungal diseases comprising administration of a therapeutically effective amount of a compound according to claim 1 to a subject in need of such treatment.

7. A method according to claim 6 wherein said fungal diseases are selected from fungal sinusitis infection and onychomycosis.

8. A pharmaceutical composition according to claim 4 which is a formulation in the form of a solution.

9. A solution according to claim 8 which is a formulation in the form of a nail lacquer.

10. The compound according to claim 1, wherein said compound is in the form of L-(−)-hydrogen malate polymorph form A, which displays principal angle of diffraction peaks by x-ray powder diffraction at about 4.0, about 8.0 and about 24.5 degrees.

11. The compound according to claim 1, wherein said compound is in the form of L-(−)-hydrogen malate polymorph form B which displays principal angle of diffraction peaks by x-ray powder diffraction at about 4.4 and about 17.3 degrees.

12. The compound according to claim 10, wherein said compound displays principal angle of diffraction peaks by x-ray powder diffraction at 4.0, 8.0 and 24.5 degrees.

13. The compound according to claim 11, wherein said compound displays principal angle of diffraction peaks by x-ray powder diffraction at 4.4 and 17.3 degrees.

* * * * *